United States Patent
Ote et al.

(10) Patent No.: US 12,249,044 B2
(45) Date of Patent: Mar. 11, 2025

(54) OCULAR FUNDUS IMAGE PROCESSING METHOD, OCULAR FUNDUS IMAGE PROCESSING DEVICE, OCULAR FUNDUS IMAGE PROCESSING PROGRAM, AND RECORDING MEDIUM HAVING SAID PROGRAM RECORDED THEREON

(71) Applicants: HAMAMATSU PHOTONICS K.K., Hamamatsu (JP); Social Welfare Corporation Seirei Social Welfare Community, Hamamatsu (JP)

(72) Inventors: Kibo Ote, Hamamatsu (JP); Fumio Hashimoto, Hamamatsu (JP); Hidenao Yamada, Hamamatsu (JP); Akira Obana, Hamamatsu (JP)

(73) Assignees: HAMAMATSU PHOTONICS K.K., Hamamatsu (JP); Social Welfare Corporation Seirei Social Welfare Community, Hamamatsu (JP)

( * ) Notice: Subject to any disclaimer, the term of this patent is extended or adjusted under 35 U.S.C. 154(b) by 376 days.

(21) Appl. No.: 17/800,062

(22) PCT Filed: Jan. 5, 2021

(86) PCT No.: PCT/JP2021/000077
§ 371 (c)(1),
(2) Date: Aug. 16, 2022

(87) PCT Pub. No.: WO2021/171788
PCT Pub. Date: Sep. 2, 2021

(65) Prior Publication Data
US 2023/0078077 A1    Mar. 16, 2023

(30) Foreign Application Priority Data
Feb. 28, 2020    (JP) ................. 2020-034202

(51) Int. Cl.
*G06T 5/50* (2006.01)
*A61B 3/12* (2006.01)
*G06T 5/00* (2006.01)

(52) U.S. Cl.
CPC ............. *G06T 5/00* (2013.01); *A61B 3/12* (2013.01); *G06T 5/50* (2013.01);
(Continued)

(58) Field of Classification Search
CPC .. G06T 5/001; G06T 5/50; G06T 2207/10024
See application file for complete search history.

(56) References Cited

U.S. PATENT DOCUMENTS

2011/0090457 A1* 4/2011 Shikaumi ............ A61B 3/14
29/428
2015/0238075 A1   8/2015 Sharifzadeh et al.

FOREIGN PATENT DOCUMENTS

| JP | 2008-110202 A | 5/2008 |
| JP | 2010-525866 A | 7/2010 |

(Continued)

OTHER PUBLICATIONS

International Preliminary Report on Patentability mailed Sep. 9, 2022 for PCT/JP2021/000077.
(Continued)

*Primary Examiner* — Sam Bhattacharya
(74) *Attorney, Agent, or Firm* — Faegre Drinker Biddle & Reath LLP

(57) ABSTRACT

An ocular fundus image processing device acquires a first image generated by irradiating an ocular fundus of a subject with excitation light of a blue wavelength and a second image generated by irradiating the ocular fundus with excitation light of a green wavelength, generates three trained models for predicting a correction factor for calculating a quantity of macular pigment of the subject from input (Continued)

images including the first image and the second image through training using three different initial values, predicts three correction factors by inputting the input images including the first image and the second image to the three trained models, calculates a statistical value of the three correction factors and derives the statistical value as the correction factor of the subject, and calculates a quantity of macular pigment of the subject on the basis of the first image and the correction factor of the subject.

16 Claims, 11 Drawing Sheets

(52) U.S. Cl.
CPC ............... *G06T 2207/10024* (2013.01); *G06T 2207/10064* (2013.01); *G06T 2207/20081* (2013.01); *G06T 2207/20224* (2013.01); *G06T 2207/30041* (2013.01)

(56) References Cited

FOREIGN PATENT DOCUMENTS

| | | |
|---|---|---|
| JP | 2015-523526 A | 8/2015 |
| JP | 2015-523546 A | 8/2015 |
| JP | 2018-000619 A | 1/2018 |
| WO | WO-2008/133693 A1 | 11/2008 |
| WO | WO-2013/163758 A1 | 11/2013 |
| WO | WO 2014/021646 A1 | 2/2014 |

OTHER PUBLICATIONS

Obana, Akira, "Grade of Cataract and Its Influence on Measurement of Macular Pigment Optical Density Using Autofluorescence Imaging," Investigative Ophthalmology & Visual Science, 2018, vol. 59, No. 7, pp. 3011-3019.

Obana, Akira, "Correction for the Influence of Cataract on Macular Pigment Measurement by Autofluorescence Technique Using Deep Learning," Trans Vis Sci Tech, 2021, Feb. 12, vol. 10, No. 2, pp. 1-11.

Sasamoto, Yuzuru, "Effect of Cataract in Evaluation of Macular Pigment Optical Density by Autofluorescence Spectrometry," Investigative Ophthalmology & Visual Science, 2011, vol. 52, No. 2, pp. 927-932.

You, Q. S., "Reproducibility of Macular Pigment Optical Density Measurement by Two-wave Length Auto-fluorescence in a Clinical Setting," Retina, 2016. vol. 37, No. 7, pp. 1381-1387.

Howells Olivia et al, "Measuring macular pigment optical density in vivo: a review of techniques", Graefe's Archive for Clinical and Experimental Ophthalmology, vol. 249, No. 3, Jan. 8, 2011, p. 315-p. 347, XP093115703.

Akuffo Kwadwo Owusu et al., "The Impact of Cataract, and Its Surgical Removal, on Measures of Macular Pigment Using the Heidelberg Spectralis HRA + OCT MultiColor Device", Investigative Opthalmology & Visual Science, vol. 57, No. 6, May 31, 2016, p. 2552, XP093116058.

* cited by examiner

OCULAR FUNDUS IMAGE PROCESSING METHOD, OCULAR FUNDUS IMAGE PROCESSING DEVICE, OCULAR FUNDUS IMAGE PROCESSING PROGRAM, AND RECORDING MEDIUM HAVING SAID PROGRAM RECORDED THEREON

TECHNICAL FIELD

An aspect of embodiments relates to an ocular fundus image processing method, an ocular fundus image processing device, an ocular fundus image processing program, and a recording medium storing the program.

BACKGROUND ART

In the related art, a device that measures a macular pigment optical density (MPOD) using autofluorescence images of a subject's ocular fundus has been used. Measurement of an MPOD indicating a macular pigment density is important for preventing age-related macular degeneration (AMD). When measurement of such an MPOD is performed on a cataract patient, an MPOD value is underestimated due to image deterioration of autofluorescence images. Therefore, it is known that a measured MPOD value needs to be corrected to acquire a true value (see Non-Patent Literature 1).

CITATION LIST

Patent Literature

[Non-Patent Literature 1] A. Obana et al., "Grade of Cataract and Its Influence on Measurement of Macular Pigment Optical Density Using Autofluorescence Imaging," Investigative Ophthalmology & Visual Science, June 2018, Vol. 59, 3011-3019

SUMMARY OF INVENTION

Technical Problem

In the correction method according to the related art, correction is performed using a method of reflecting a correction factor derived through subjective evaluation in a measured value of the MPOD and a method based on multiple regression. However, such a technique has a problem in that a correction process is troublesome and reliability of the corrected MPOD is not satisfactory.

Therefore, an aspect of embodiments was invented in consideration of the aforementioned circumstances, and an objective thereof is to provide an ocular fundus image processing method, an ocular fundus image processing device, an ocular fundus image processing program, and a recording medium storing the program that can derive an MPOD with high reliability through a simple process.

Solution to Problem

According to an aspect of embodiments, there is provided an ocular fundus image processing method including: a step of acquiring a first image which is a fluorescence image of an ocular fundus of a subject generated by irradiating the ocular fundus with excitation light of a first wavelength; a step of acquiring a second image which is a fluorescence image of the ocular fundus of the subject generated by irradiating the ocular fundus with excitation light of a second wavelength different from the first wavelength; a step of generating a plurality of trained deep learning models for predicting a correction factor for calculating a quantity of macular pigment of the subject from input images including at least the first image and the second image through training using a plurality of different initial values; a step of predicting a plurality of correction factors by inputting the input images including at least the first image and the second image to the plurality of trained deep learning models; a step of calculating a statistical value of the plurality of correction factors and deriving the statistical value as the correction factor of the subject; and a step of calculating a quantity of macular pigment of the subject on the basis of at least one of the first image and the second image and the correction factor of the subject.

Alternatively, according to another aspect of the embodiments, there is provided an ocular fundus image processing device including: a first acquisition unit configured to acquire a first image which is a fluorescence image of an ocular fundus of a subject generated by irradiating the ocular fundus with excitation light of a first wavelength; a second acquisition unit configured to acquire a second image which is a fluorescence image of the ocular fundus of the subject generated by irradiating the ocular fundus with excitation light of a second wavelength different from the first wavelength; a generation unit configured to generate a plurality of trained deep learning models for predicting a correction factor for calculating a quantity of macular pigment of the subject from input images including at least the first image and the second image through training using a plurality of different initial values; a prediction unit configured to predict a plurality of correction factors by inputting the input images including at least the first image and the second image to the plurality of trained deep learning models; a derivation unit configured to calculate a statistical value of the plurality of correction factors and to derive the statistical value as the correction factor of the subject; and a calculation unit configured to calculate a quantity of macular pigment of the subject on the basis of at least one of the first image and the second image and the correction factor of the subject.

Alternatively, according to another aspect of the embodiments, there is provided an ocular fundus image processing program causing a processor to serve as: a first acquisition unit configured to acquire a first image which is a fluorescence image of an ocular fundus of a subject generated by irradiating the ocular fundus with excitation light of a first wavelength; a second acquisition unit configured to acquire a second image which is a fluorescence image of the ocular fundus of the subject generated by irradiating the ocular fundus with excitation light of a second wavelength different from the first wavelength; a generation unit configured to generate a plurality of trained deep learning models for predicting a correction factor for calculating a quantity of macular pigment of the subject from input images including at least the first image and the second image through training using a plurality of different initial values; a prediction unit configured to predict a plurality of correction factors by inputting the input images including at least the first image and the second image to the plurality of trained deep learning models; a derivation unit configured to calculate a statistical value of the plurality of correction factors and to derive the statistical value as the correction factor of the subject; and a calculation unit configured to calculate a quantity of macular pigment of the subject on the basis of at least one of the first image and the second image and the correction factor of the subject.

Alternatively, according to another aspect of the embodiments, there is provided a computer-readable recording medium storing the aforementioned ocular fundus image processing program.

According to any one of the aforementioned aspects, a first image which is a fluorescence image of an ocular fundus of a subject obtained using excitation light of a first wavelength and a second image which is a fluorescence image of the ocular fundus of the subject obtained using excitation light of a second wavelength are acquired, and a plurality of trained deep learning models for predicting a correction factor from input images including the first image and the second image is generated using a plurality of different initial values. A plurality of correction factors is predicted by inputting the input images including the first image and the second image to the plurality of trained deep learning models, a statistical value of the plurality of correction factors is derived as the correction factor of the subject, and a quantity of macular pigment of the subject is calculated on the basis of the first image or the second image and the correction factor of the subject. Accordingly, a plurality of deep learning models is constructed using the first image and the second image as training data, the plurality of correction factors is predicted by inputting the first image and the second image of the subject to the plurality of deep learning models, and the quantity of macular pigment is calculated by statistically evaluating the plurality of correction factors. As a result, it is possible to calculate a quantity of macular pigment with high reliability in which a trend of change in image quality of a plurality of images of the subject is reflected through a simple process.

Advantageous Effects of Invention

According to the embodiments, it is possible to derive an MPOD with high reliability through a simple process.

DESCRIPTION OF EMBODIMENTS

Hereinafter, an embodiment of the present invention will be described in detail with reference to the accompanying drawings. In the following description, the same elements or elements having the same functions will be referred to by the same reference signs, and description thereof will not be repeated.

Figure 1:
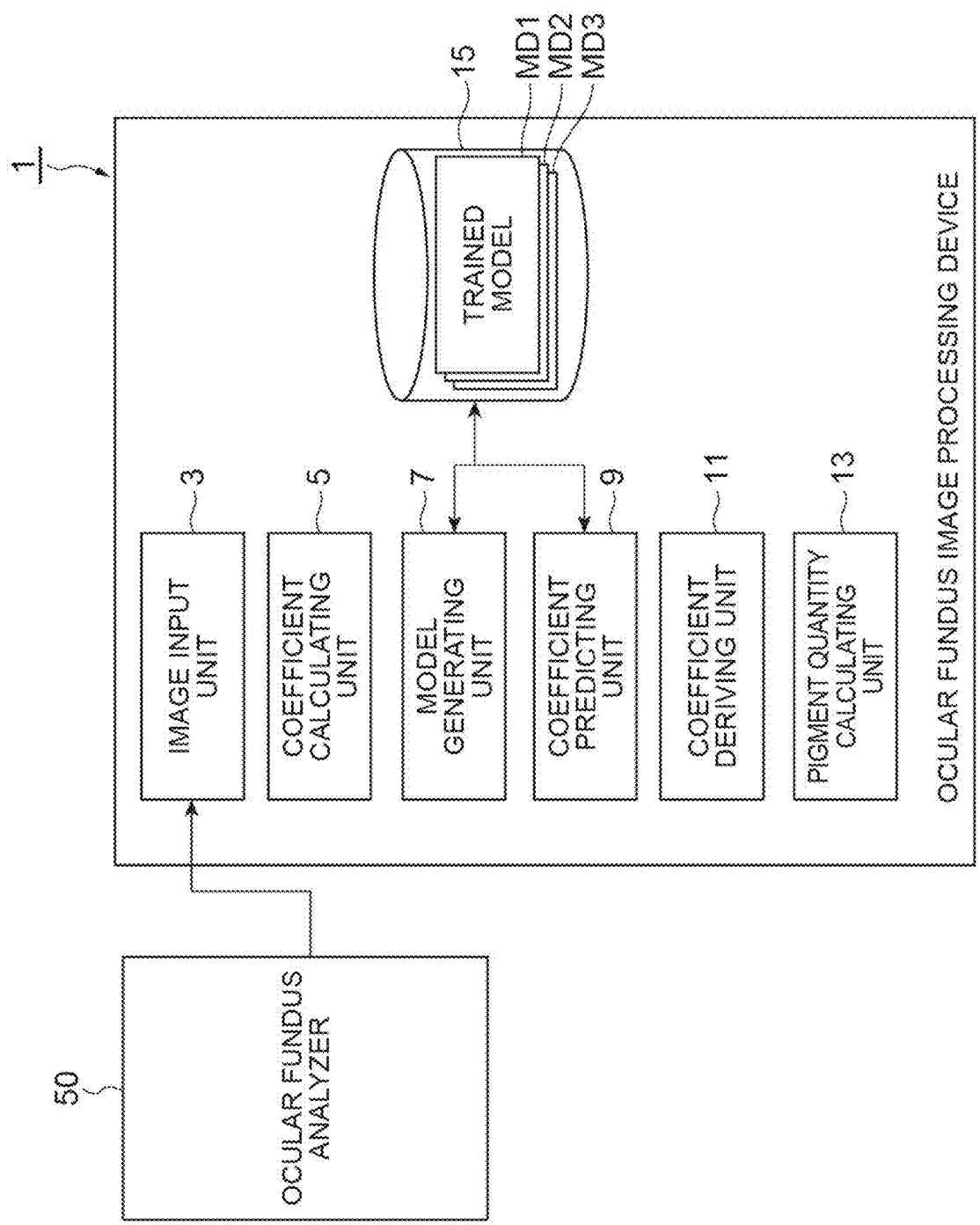
FIG. 1 is a block diagram illustrating a functional configuration of an ocular fundus image processing device 1 according to an embodiment.

FIG. 1 is a block diagram illustrating a functional configuration of an ocular fundus image processing device 1 according to an embodiment. As illustrated in FIG. 1, the ocular fundus image processing device 1 is an arithmetic device that estimates a macular pigment optical density (MPOD) indicating a quantity of macular pigment of a subject by processing ocular fundus images of the subject acquired by an external ocular fundus analyzer 50. The ocular fundus image processing device 1 can acquire ocular fundus images from the external ocular fundus analyzer 50 via a wired or wireless communication network.

The ocular fundus analyzer 50 is a known optical device that acquires an ocular fundus image of a subject, includes a light source and an imaging device which are not illustrated, and has a function of irradiating an ocular fundus of a subject with excitation light and acquiring an autofluorescence image of an ocular fundus generated in response thereto as an ocular fundus image. In this embodiment, the ocular fundus analyzer 50 acquires a first ocular fundus image obtained by irradiating a subject with excitation light of a blue wavelength 486 nm and a second ocular fundus image obtained by irradiating the subject with excitation light of a green wavelength 518 nm. The wavelength of the excitation light used to acquire the first ocular fundus image is in a range of 450 nm to 495 nm which is a blue wavelength band, and the wavelength of the excitation light used to acquire the second ocular fundus image is in a range of 495 nm to 570 nm which is a green wavelength band.

In general, since a yellow spot located at the center of a retina has characteristics of absorbing blue light, a change of a luminance distribution based on a quantity of macular pigment appears in an ocular fundus image of a subject acquired by the ocular fundus analyzer 50. In the related art, an MPOD is calculated by calculating a ratio of a luminance value in the vicinity of the center (fovea centralis) of a retina and a mean value of luminance values in a circular region centered thereon on the basis of an autofluorescence image acquired through excitation of blue light.

The ocular fundus image processing device 1 estimates an MPOD on the basis of the first ocular fundus image and the second ocular fundus image acquired from a subject by the ocular fundus analyzer 50. That is, the ocular fundus image processing device 1 includes an image input unit (a first acquisition unit, a second acquisition unit) 3, a coefficient calculating unit 5, a model generating unit 7, a coefficient predicting unit 9, a coefficient deriving unit 11, a pigment quantity calculating unit 13, and a model storage unit 15 as functional elements.

Figure 2:
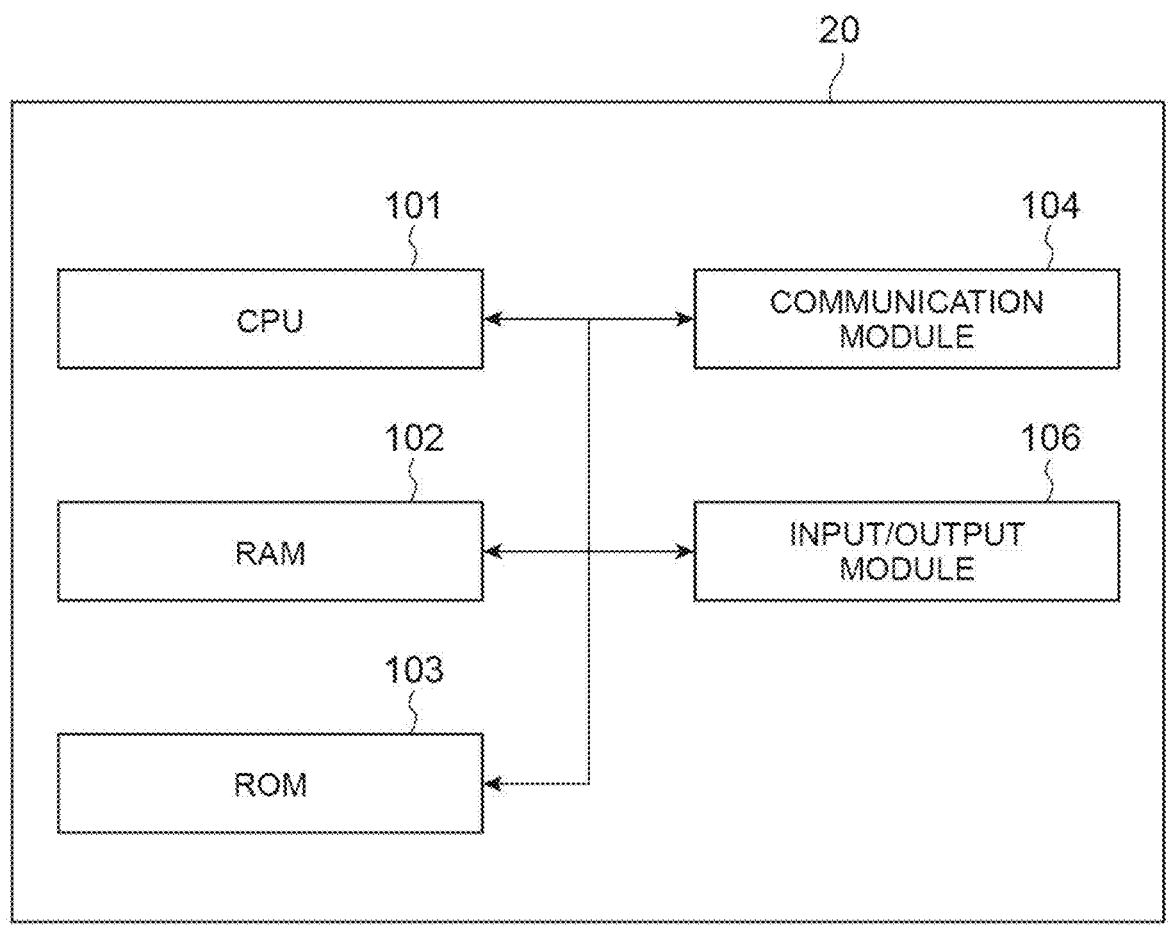
FIG. 2 is a block diagram illustrating an example of a hardware configuration of a computer 20 which is used as the ocular fundus image processing device 1 illustrated in FIG. 1.

FIG. 2 illustrates a hardware configuration of a computer 20 that realizes the ocular fundus image processing device 1 according to this embodiment. As illustrated in FIG. 2, the computer 20 is physically a computer including a central processing unit (CPU) 101 which is a processor, a random access memory (RAM) 102 and a read only memory (ROM) 103 which are recording media, a communication module 104, and an input/output module 106, which are electrically connected to each other. The computer 20 may include a display, a keyboard, a mouse, and a touch panel display as the input/output module 106, and may include a data recording device such as a hard disk drive or a semiconductor memory. The computer 20 may include a plurality of computers. The computer 20 may further include a graphics processing unit (GPU) which is a processor specialized in image processing or may be configured to enable parallel processing in the CPU 101 and the GPU.

The functional units of the ocular fundus image processing device 1 illustrated in FIG. 1 are realized by reading a program (an ocular fundus image processing program in this embodiment) to hardware such as the CPU 101 and the RAM 102, operating the communication module 104 and the input/output module 106 under the control of the CPU 101, and performing reading and writing of data with respect to the RAM 102. The CPU 101 of the computer 20 causes the computer 20 to serve as the functional units illustrated in FIG. 1 by executing a computer program, and sequentially performs processes corresponding to an ocular fundus image processing method which will be described later. Various types of data required to execute the computer program and various types of data generated by executing the computer program are all stored in a built-in memory such as the ROM 103 or the RAM 102 or a storage medium such as a hard disk drive.

Details of the functions of the functional units of the ocular fundus image processing device 1 will be described below.

The image input unit 3 acquires a first ocular fundus image and a second ocular fundus image (hereinafter referred to as an ocular fundus image set of a prediction target) of a subject on whom cataract surgery has not been performed in a prediction phase of estimating an MPOD of the subject. In a training phase of generating a plurality of trained deep learning models, the image input unit 3 acquires a plurality of combinations (for example, 148 combinations) of a first ocular fundus image and a second ocular fundus image of a subject on whom cataract surgery has not been performed (hereinafter also referred to as a pre-surgery ocular fundus image set) and a first ocular fundus image and a second ocular fundus image of the subject on whom cataract surgery has been performed (hereinafter also referred to as a post-surgery ocular fundus image set) as training data used for training with respect to various subjects or under various imaging conditions. When the ocular fundus image set of the prediction target and the pre-surgery ocular fundus image set are acquired, the image input unit 3 calculates a difference between pixel values of the images on the basis of the first ocular fundus image and the second ocular fundus image included in each ocular fundus image set, generates a difference image in which luminance values of all pixels are shifted such that a minimum value of the luminance value difference becomes zero, and adds the generated difference image to each ocular fundus image set.

The coefficient calculating unit 5 calculates a correction factor (CF) value which is a correction coefficient for correcting the MPOD for each combination on the basis of a plurality of combinations of the pre-surgery ocular fundus image set and the post-surgery ocular fundus image set in the training phase.

Specifically, the coefficient calculating unit 5 calculates an MPOD with reference to at least one ocular fundus image (preferably the first ocular fundus image) in the pre-surgery ocular fundus image set. The MPOD is calculated using the following expression on the basis of a ratio of a luminance value $I_{min}$ at a prescribed pixel position in the vicinity of the center of a retina and a mean value $I_{max(ave)}$ of luminance values in a prescribed circular region centered thereon.

$$MPOD = -1.4 \cdot \log\{I_{min}/I_{max(ave)}\}$$

The coefficient calculating unit 5 calculates the MPOD at positions of eccentricities 0.23 degrees, 0.51 degrees, 0.98 degrees, and 1.99 degrees from the center (fovea centralis) of a retina and defines the calculated MPOD values as local $MPOD_{0.23}$, local $MPOD_{0.51}$, local $MPOD_{0.98}$, and local $MPOD_{1.99}$. The coefficient calculating unit 5 calculates a sum of the MPOD values in a region within the eccentricity 8.98 degrees from the center (fovea centralis) of the retina and defines the calculated sum as an MPOD volume. The coefficient calculating unit 5 sets a set of the calculated MPOD values {local $MPOD_{0.23}$, local $MPOD_{0.51}$, local $MPOD_{0.98}$, local $MPOD_{1.99}$, MPOD volume} as an MPOD numerical value sequence.

Similarly, the coefficient calculating unit 5 calculates the MPOD numerical value sequence with reference to at least one ocular fundus image (preferably the first ocular fundus image) in the post-surgery ocular fundus image set.

The coefficient calculating unit 5 calculates a CF value for correction from a pre-surgery MPOD numerical value sequence to a post-surgery MPOD numerical value sequence on the basis of an MPOD numerical value sequence calculated using the pre-surgery ocular fundus image set (a pre-surgery MPOD numerical value sequence) and an MPOD numerical value sequence calculated using the post-surgery ocular fundus image set (a post-surgery MPOD numerical value sequence). For example, a set of CF values $\{CF_{0.23}, CF_{0.51}, CF_{0.98}, CF_{1.99}, CF_{TOTAL}\}$ (hereinafter a CF numerical value sequence) is calculated by dividing the post-surgery MPOD numerical value sequence by the pre-surgery MPOD numerical value sequence.

The coefficient calculating unit 5 adds a plurality of sets of CF numerical value sequences calculated as described above to a plurality of corresponding pre-surgery ocular fundus image sets used as training data in the model generating unit 7, and delivers the added sets to the model generating unit 7. The CF numerical value sequence is used as training data (a label) in training (supervised training) in the model generating unit 7.

In the training phase, the model generating unit 7 generates a plurality of trained deep learning models for predicting a CF numerical value sequence indicating a correction factor for calculating a quantity of macular pigment of a subject using at least one image in an ocular fundus image set of a prediction target which is the subject as an input image through training using a plurality of pre-surgery ocular fundus image sets. Specifically, the model generating unit 7 generates three trained models having a convolutional neural network (CNN) structure for predicting a CF numerical value sequence using a first ocular fundus image, a second ocular fundus image and a difference image included in an ocular fundus image set of a prediction target as input images, and stores data MD1, MD2, and MD3 including parameters for operating the three generated trained models in the model storage unit 15.

Figure 3:
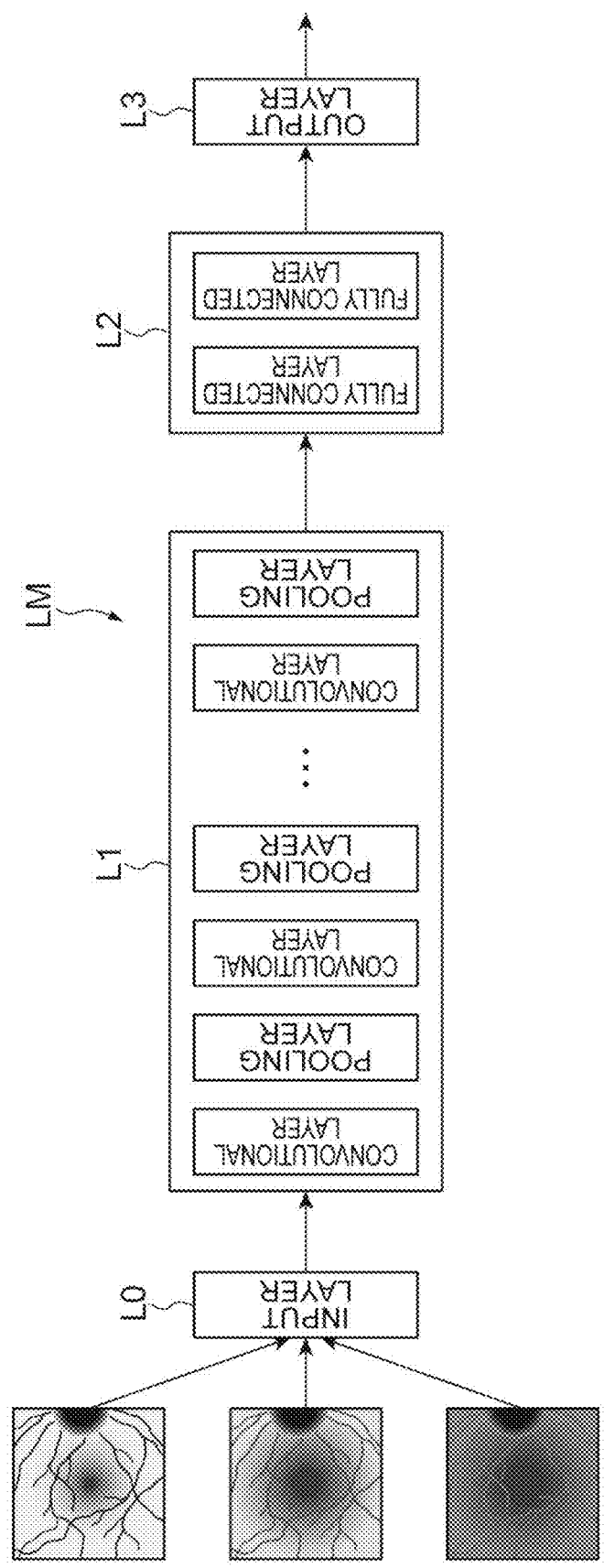
FIG. 3 is a diagram illustrating a network structure of a trained model LM which is generated by a model generating unit 7 illustrated in FIG. 1.

FIG. 3 illustrates a network structure of trained models LM generated by the model generating unit 7. A trained model LM includes an input layer L0 to which an ocular fundus image set of a prediction target is input by 3ch, a preceding-stage structure L1 in which a plurality of sets of a convolutional layer and a pooling layer is alternately connected to each other in a stage subsequent to the input layer L0, a subsequent-stage structure L2 including two fully connected layers sequentially connected to the back of the preceding-stage structure L1, and an output layer L3 that converts data of each node from the subsequent-stage structure L2 to a final CF numerical value sequence and outputs the resultant as a primary vector. As such a trained model LM, a model in which the number of nodes of the output layer L3 is changed to a desired number (5 in this embodiment) using the structure of the CNN trained with a large-scale image database such as ImageNet as a base can be used. Parameters trained already (such as parameters of a weighting filter) are used as initial values in the parameters of the trained model LM (transfer learning is applied as the premise), except for a fully connected layer in the most subsequent stage.

Figure 4:
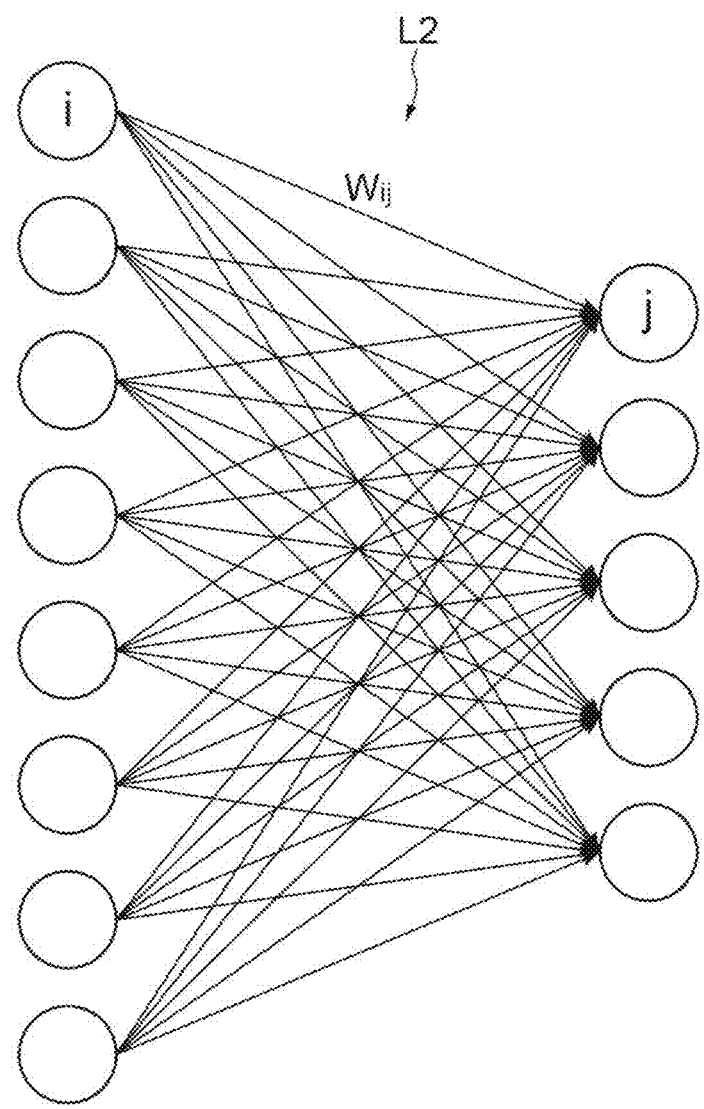
FIG. 4 is a diagram illustrating a connecting configuration of two fully connected layers in a subsequent-stage structure L2 of the trained model LM illustrated in FIG. 3.

The model generating unit 7 generates three trained models through training based on three different initial values using a plurality of pre-surgery ocular fundus image sets as training data and using CF numerical value sequences corresponding thereto as training data. That is, before the training, the model generating unit 7 generates a pseudo-random number sequence by inputting three random number seeds which are three preset initial values to a pseudo-random number generator provided in the computer 20 and initializes parameters of the fully connected layer in the most subsequent stage in the trained model LM of the CNN on the basis of the generated pseudo-random number sequence. For example, as illustrated in FIG. 4, an initial value of a coupling weighting $w_{i,j}$ between node i and node j (where i and j are arbitrary integers) in two fully connected layers of the subsequent-stage structure L2 of the trained model LM is set depending on the pseudo-random number sequence. Since optimization results of three trained models generated by training depend on the initial values due to this random initialization of the trained model LM, the prediction results using three trained models become slightly different.

The model generating unit 7 may randomly change the order of presenting training data on the basis of the pseudo-random number sequence in each loop (each epoch) in which all training data is presented (input) to the trained model LM instead of initialization of parameters of the trained model LM based on the pseudo-random number sequence or in addition to initialization of the parameters. Accordingly, it is possible to prevent parameters of a trained model from falling into local solutions at the time of training. When a trained model which is a CNN is trained, data augmentation of cropping a random position in the vicinity of the center of a presented input image and increasing variation of the input image can be performed, and an effect of data augmentation can also be changed between three trained models on the basis of the function of the model generating unit 7.

In the prediction phase, the coefficient predicting unit 9 predicts three sets of CF numerical value sequences of a subject by inputting pre-surgery ocular fundus image set of a subject using three trained models generated in the training phase. At this time, the coefficient predicting unit 9 reads data MD1, MD2, and MD3 required to perform a prediction process using three trained models from the model storage unit 15.

In the prediction phase, the coefficient deriving unit 11 calculates a statistical value of the three sets of CF numerical value sequences predicted for a subject by the coefficient predicting unit 9 and derives the statistical value as a final CF numerical value sequence of the subject. For example, the coefficient deriving unit 11 calculates mean values $\{CFA_{0.23}, CFA_{0.51}, CFA_{0.98}, CFA_{1.99}, CFA_{TOTAL}\}$ of numerical values of the three sets of CF numerical value sequences $\{CF_{0.23}, CF_{0.51}, CF_{0.98}, CF_{1.99}, CF_{TOTAL}\}$ and sets a numerical value sequence of the calculated mean values as the final CF numerical value sequence. By setting a mean value of predicted values as a final predicted value in this way (performing an ensemble process), it is possible to curb dependency of the optimization result of deep learning on the initial values and to achieve improvement of prediction accuracy of the correction values.

In the prediction phase, the pigment quantity calculating unit 13 calculates the MPOD numerical value sequence of the subject using the final CF numerical value sequence derived by the coefficient deriving unit 11 and outputs the calculated MPOD numerical value sequence to the input/output module 106 (FIG. 2). The pigment quantity calculating unit 13 may transmit the calculated MPOD numerical value sequence to an external device via the communication module 104 (FIG. 2). That is, the pigment quantity calculating unit 13 calculates an MPOD numerical value sequence using the same calculation method as in the coefficient calculating unit 5 with reference to at least one ocular fundus image (preferably, the first ocular fundus image) in the ocular fundus image sets of the prediction target which is a subject. Then, the pigment quantity calculating unit 13 calculates an MPOD numerical value sequence of the subject by correcting the calculated MPOD numerical value sequence using the CF numerical value sequence. At this time, the pigment quantity calculating unit 13 calculates the MPOD numerical value sequence of the subject by multiplying the numerical values included in the MPOD numerical value sequence $\{$local $MPOD_{0.23}$, local $MPOD_{0.51}$, local $MPOD_{0.98}$, local $MPOD_{1.99}$, MPOD volume$\}$ by the corresponding correction values included in the CF numerical value sequence $\{CFA_{0.23}, CFA_{0.51}, CFA_{0.98}, CFA_{1.99}, CFA_{TOTAL}\}$.

Figure 5:
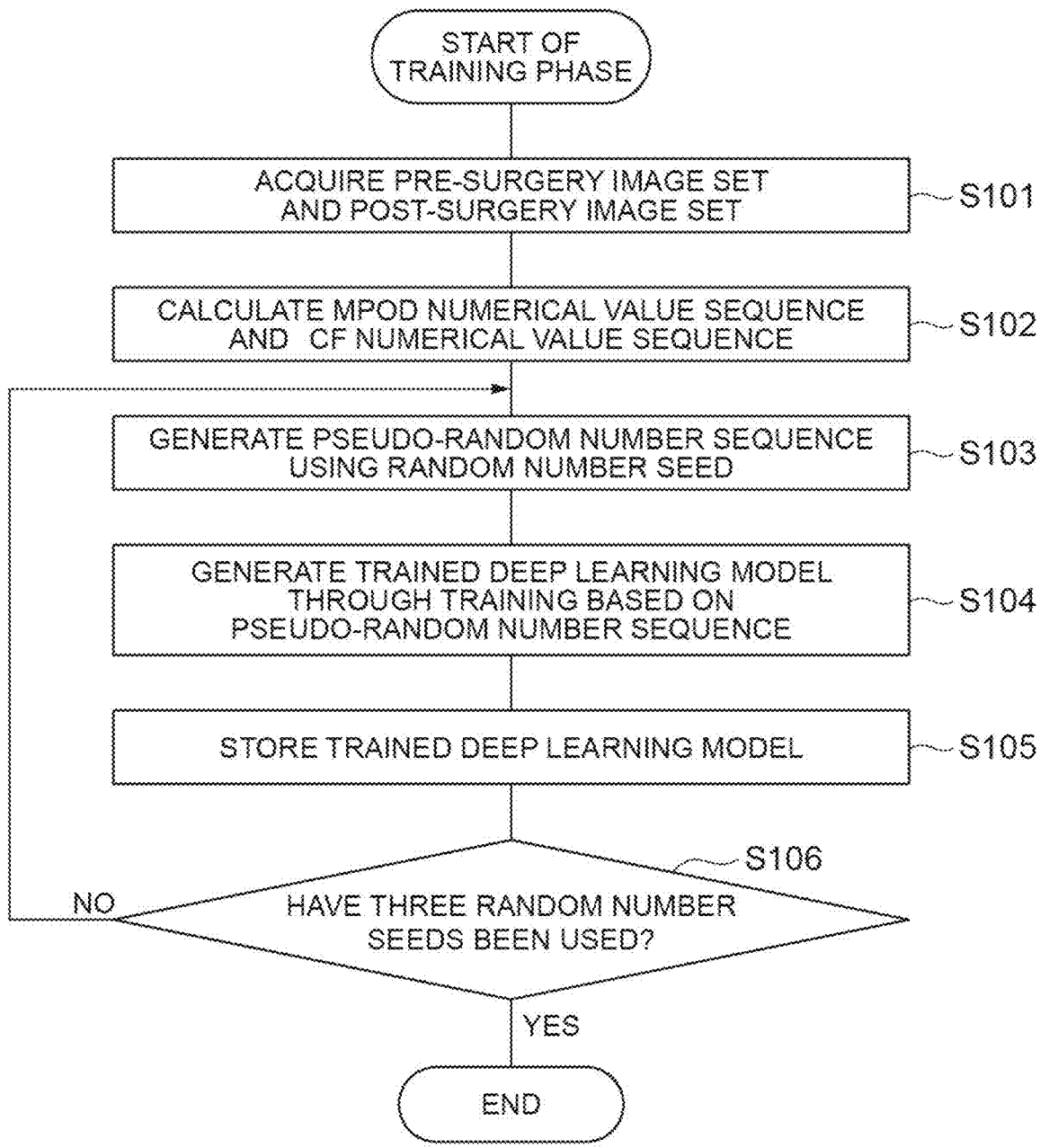
FIG. 5 is a flowchart illustrating a routine of a training phase which is performed by the ocular fundus image processing device 1.
Figure 6:
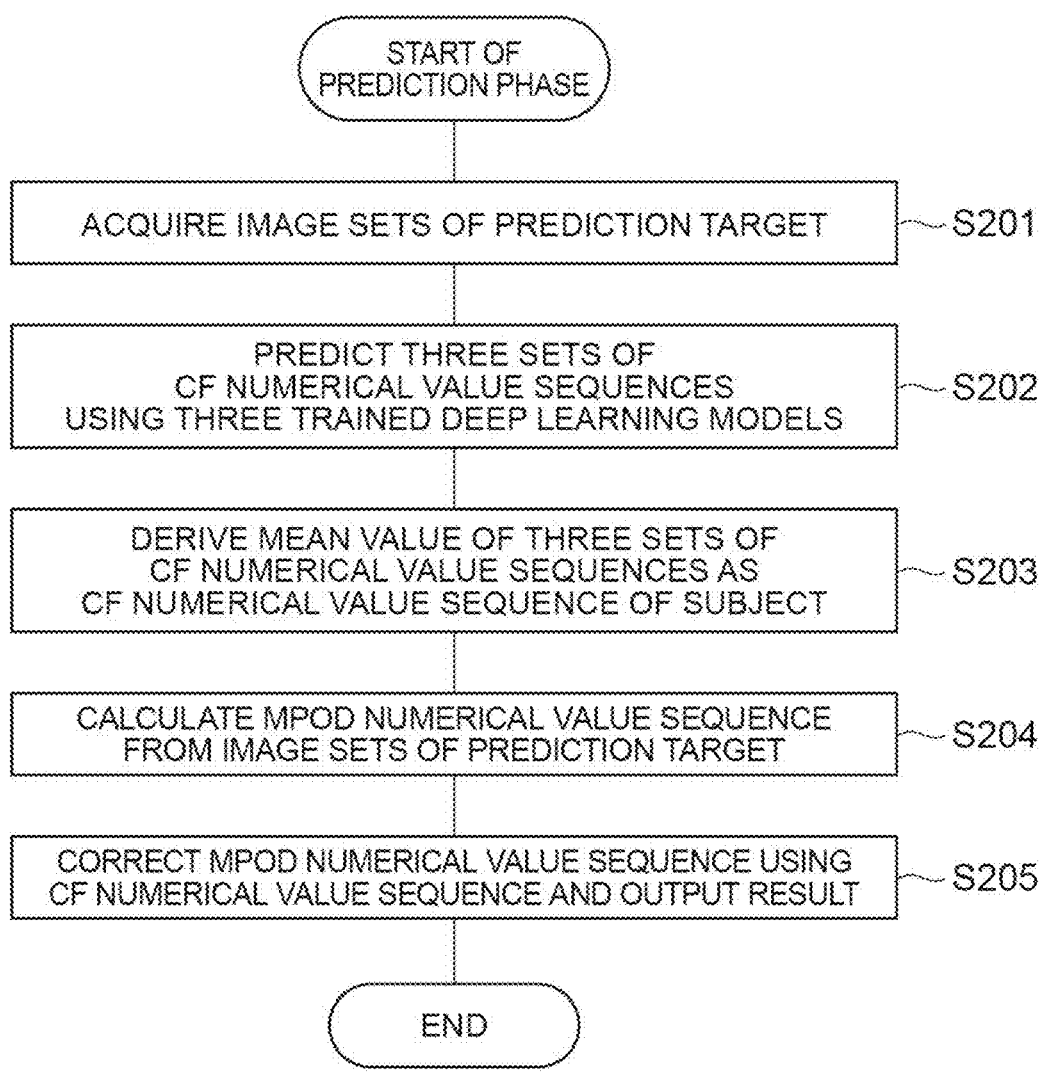
FIG. 6 is a flowchart illustrating a routine of a prediction phase which is performed by the ocular fundus image processing device 1.

A routine of processes of predicting an MPOD of a subject using the ocular fundus image processing device 1 according to this embodiment, that is, a flow of an ocular fundus image processing method according to this embodiment, will be described below. FIG. 5 is a flowchart illustrating a routine of the training phase which is performed by the ocular fundus image processing device 1. FIG. 6 is a flowchart illustrating a routine of the prediction phase which is performed by the ocular fundus image processing device 1.

First, when the training phase is started in accordance with an instruction or the like input by an operator of the ocular fundus image processing device 1, the image input unit 3 acquires a plurality of sets of a pre-surgery ocular fundus image set and a post-surgery ocular fundus image set (Step S101). Accordingly, the coefficient calculating unit 5 calculates the MPOD numerical value sequence for each of the pre-surgery ocular fundus image set and the post-surgery ocular fundus image set and calculates the CF numerical value sequence on the basis of the calculated numerical value sequence (Step S102). Calculation of the CF numerical value sequence is repeatedly performed on all the sets of the pre-surgery ocular fundus image set and the post-surgery ocular fundus image set, and the calculated CF numerical value sequences are added as training data to a corresponding pre-processing ocular fundus image set.

Then, the model generating unit 7 generates a pseudo-random number using a preset random number seed (Step S103). Then, the model generating unit 7 generates a trained deep learning model through training by setting initial values of the CNN on the basis of the pseudo-random number and changing the presentation order of training data on the basis of the pseudo-random number (Step S104). The model generating unit 7 stores data of the generated trained deep learning model in the model storage unit 15 (Step S105).

By repeatedly performing the processes of Steps S103 to S105 three times while three random number seeds are set (Step S106), three trained deep learning models are generated and stored.

Then, when the prediction phase for a subject is started in accordance with an instruction or the like input by an operator of the ocular fundus image processing device 1, the image input unit 3 acquires an ocular fundus image set of a prediction target which is the subject (Step S201). Then, the coefficient predicting unit 9 predicts three sets of CF numerical value sequences by inputting the ocular fundus image set of the prediction target as input images to the three trained deep learning models (Step S202).

The coefficient deriving unit 11 derives a final CF numerical value sequence of the subject by calculating a statistical value of the predicted three sets of CF numerical value sequences (Step S203). Thereafter, the pigment quantity calculating unit 13 calculates an MPOD numerical value sequence on the basis of the first ocular fundus image and the second ocular fundus image included in the ocular fundus image set of the prediction target (Step S204). Finally, the pigment quantity calculating unit 13 corrects the MPOD numerical value sequence using the CF numerical value sequence and outputs the corrected MPOD numerical value sequence (Step S205).

Figure 7:
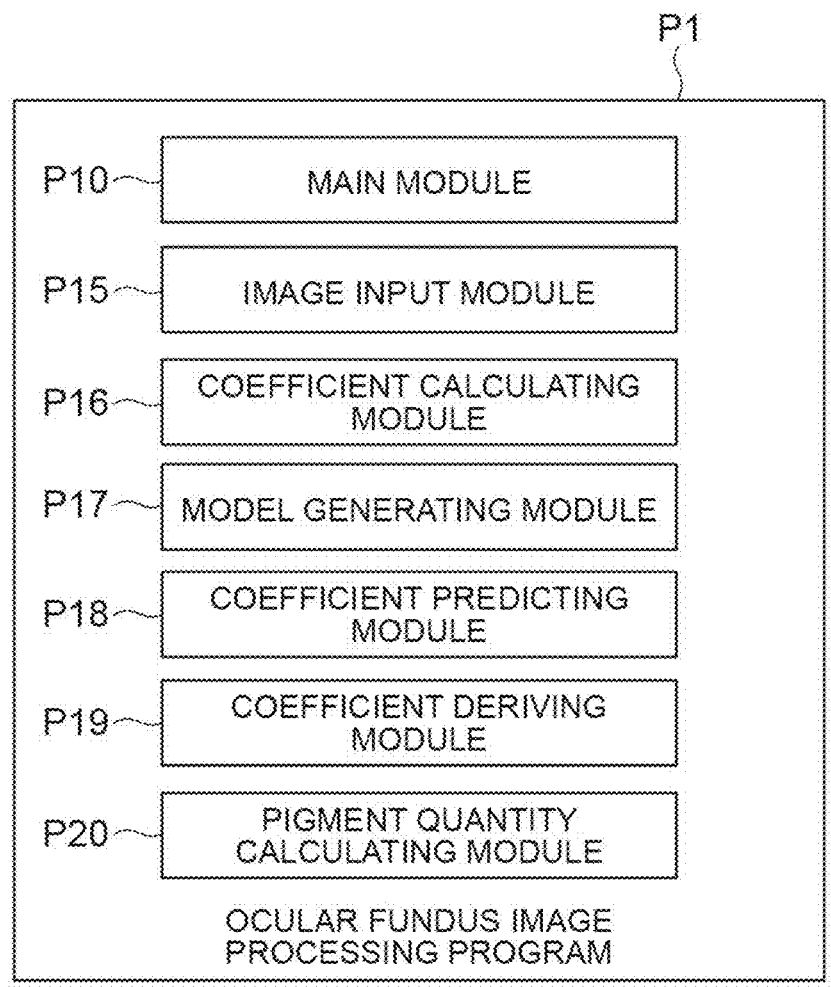
FIG. 7 is a diagram illustrating a configuration of an ocular fundus image processing program according to the embodiment.

A configuration of an ocular fundus image processing program causing the computer 20 to serve as the ocular fundus image processing device 1 will be described below with reference to FIG. 7.

The ocular fundus image processing program P1 includes a main module P10, an image input module P15, a coefficient calculating module P16, a model generating module P17, a coefficient predicting module P18, a coefficient deriving module P19, and a pigment quantity calculating module P20.

The main module P10 is a part that integrally controls processing of an ocular fundus image. The functions which are realized by executing the image input module P15, the coefficient calculating module P16, the model generating module P17, the coefficient predicting module P18, the coefficient deriving module P19, and the pigment quantity calculating module P20 are the same as the functions of the image input unit 3, the coefficient calculating unit 5, the model generating unit 7, the coefficient predicting unit 9, the coefficient deriving unit 11, and the pigment quantity calculating unit 13 of the ocular fundus image processing device 1.

The ocular fundus image processing program P1 is provided, for example, using a recording medium such as a CD-ROM, a DVD, or a ROM or a semiconductor memory. The ocular fundus image processing program P1 may be provided as a computer data signal superimposed on carrier waves via a network.

With the ocular fundus image processing device 1, a plurality of sets of a first ocular fundus image obtained using excitation light of a blue wavelength band and a second ocular fundus image obtained using excitation light of a green wavelength band are acquired, and three trained deep learning models for predicting a CF numerical value sequence from input images including the first ocular fundus image and the second ocular fundus image are generated using three different initial values. Three CF numerical value sequences are predicted by inputting the input images including the first ocular fundus image and the second ocular fundus image for a subject on whom a cataract surgery has not been performed to the three trained deep learning models, a mean value which is a statistical value of the three CF numerical value sequences is derived as a final CF numerical value sequence of the subject, and an MPOD numerical value sequence of a subject is calculated on the basis of an MPOD numerical value sequence calculated from the first ocular fundus image and the second ocular fundus image and the CF numerical value sequence. Accordingly, three deep learning models are constructed using the first ocular fundus image and the second ocular fundus image as training data, three CF numerical value sequences are predicted by inputting the first ocular fundus image and the second ocular fundus image of the subject to the three deep learning models, and a quantity of macular pigment is calculated by statistically evaluating the three CF numerical value sequences. As a result, it is possible to calculate a quantity of macular pigment with high reliability in which a trend of change in image quality of a plurality of images of the subject is reflected through a simple process.

Particularly, in this embodiment, the training phase is performed while changing the random number seed. In this case, initialization of parameters of a CNN, the presentation order of training data, an effect of data augmentation, and the like vary depending on the random number seeds. Since optimal initial values of parameters of a CNN, the optimal presentation order of training data, or the optimal method of data augmentation are unknown, it is possible to obtain a predicted value close to a prediction result of the CNN when optimal training is performed by calculating a mean value of predicted values of the trained CNN which has been trained using various training seeds.

In this embodiment, excitation light of a wavelength in a blue wavelength band is used to acquire the first ocular fundus image, and excitation light of a wavelength in a green wavelength band is used to acquire the second ocular fundus image. Since a yellow spot has characteristics of absorbing blue light, it is possible to calculate a quantity of macular pigment with high accuracy by using two images generated by excitation light of such wavelengths as input images.

In this embodiment, the input images input to the CNN include a difference image. In this case, it is possible to calculate a quantity of macular pigment with higher accuracy.

In this embodiment, a mean value of three predicted values which are predicted using three trained deep learning models is calculated as a statistical value. In this case, since the quantity of macular pigment can be calculated such that the predicted values predicted using the three trained deep learning models are equally reflected, it is possible to calculate a quantity of macular pigment with higher reliability.

In this embodiment, the deep learning models are trained using pseudo-random numbers generated from three random number seeds. With this configuration, it is possible to comprehensively generate three deep learning models for predicting the CF numerical value sequences even when training is performed using a restricted number of input images.

In this embodiment, pseudo-random numbers are used to initialize parameters of a deep learning model or used to change the order of input images which are input to a deep learning model. With this configuration, it is possible to comprehensively generate a plurality of deep learning models for predicting CF numerical value sequences even when training is performed using a restricted number of input images. As a result, it is possible to enhance accuracy in predicting a quantity of macular pigment on the basis of a statistical value.

A result of experiment for accuracy of an MPOD numerical value sequence predicted in this embodiment will be described below.

Figure 8:
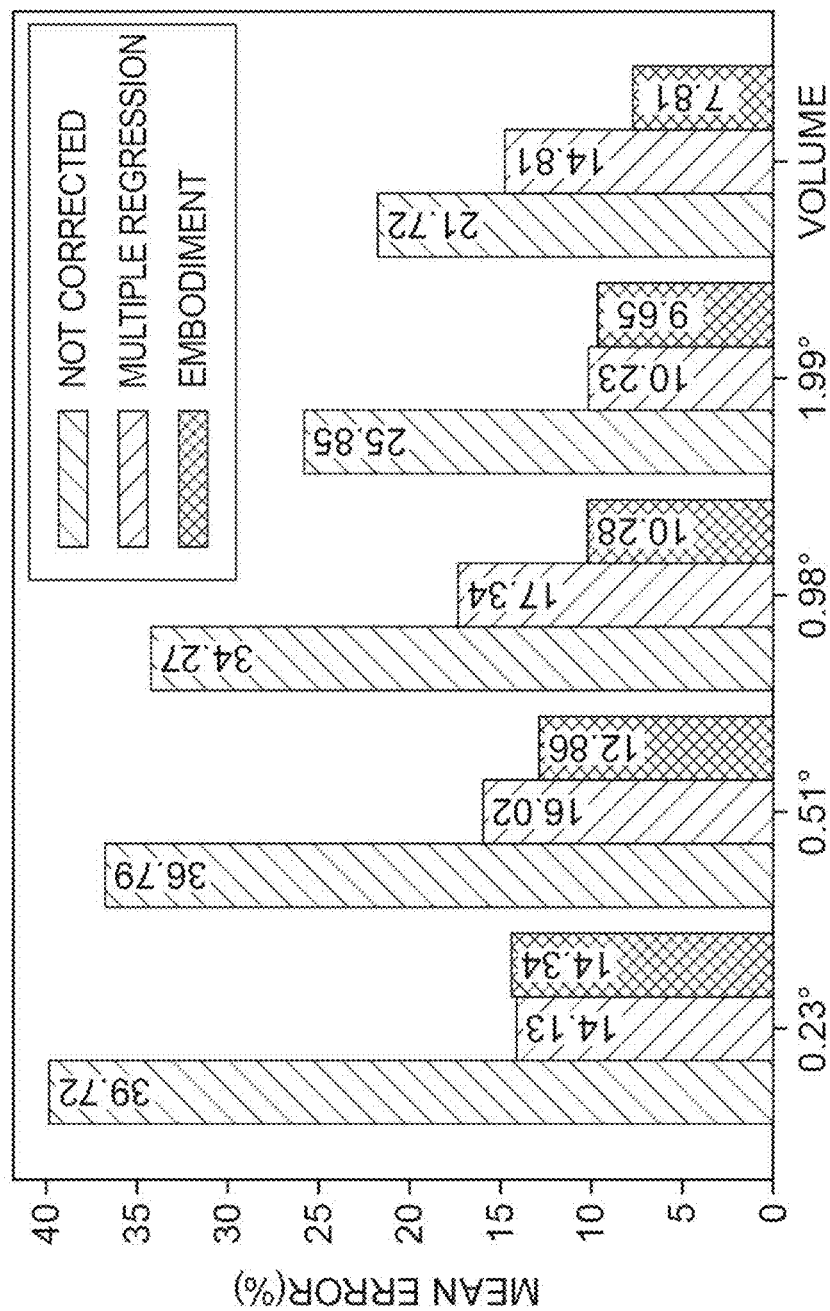
FIG. 8 is a graph illustrating a result of an experiment on accuracy of an MPOD numerical value sequence predicted in the embodiment.

FIG. 8 illustrates mean errors of numerical values {local $MPOD_{0.23}$, local $MPOD_{0.51}$, local $MPOD_{0.98}$, local $MPOD_{1.99}$, MPOD volume} included in the MPOD numerical value sequence predicted in this embodiment in comparison with a case in which correction using a CF numerical value sequence is not performed and a case in which correction using the method of multiple regression according to the related art (described in "A. Obana et al., "Grade of Cataract and Its Influence on Measurement of Macular Pigment Optical Density Using Autofluorescence Imaging," Investigative Ophthalmology & Visual Science, June 2018, Vol. 59, 3011-3019") is performed. In this way, according to this embodiment, it can be seen that errors were improved as a whole in comparison with the method using multiple regression. Particularly, the error of the MPOD volume was greatly improved from 14.81% to 7.81%.

Figure 9:
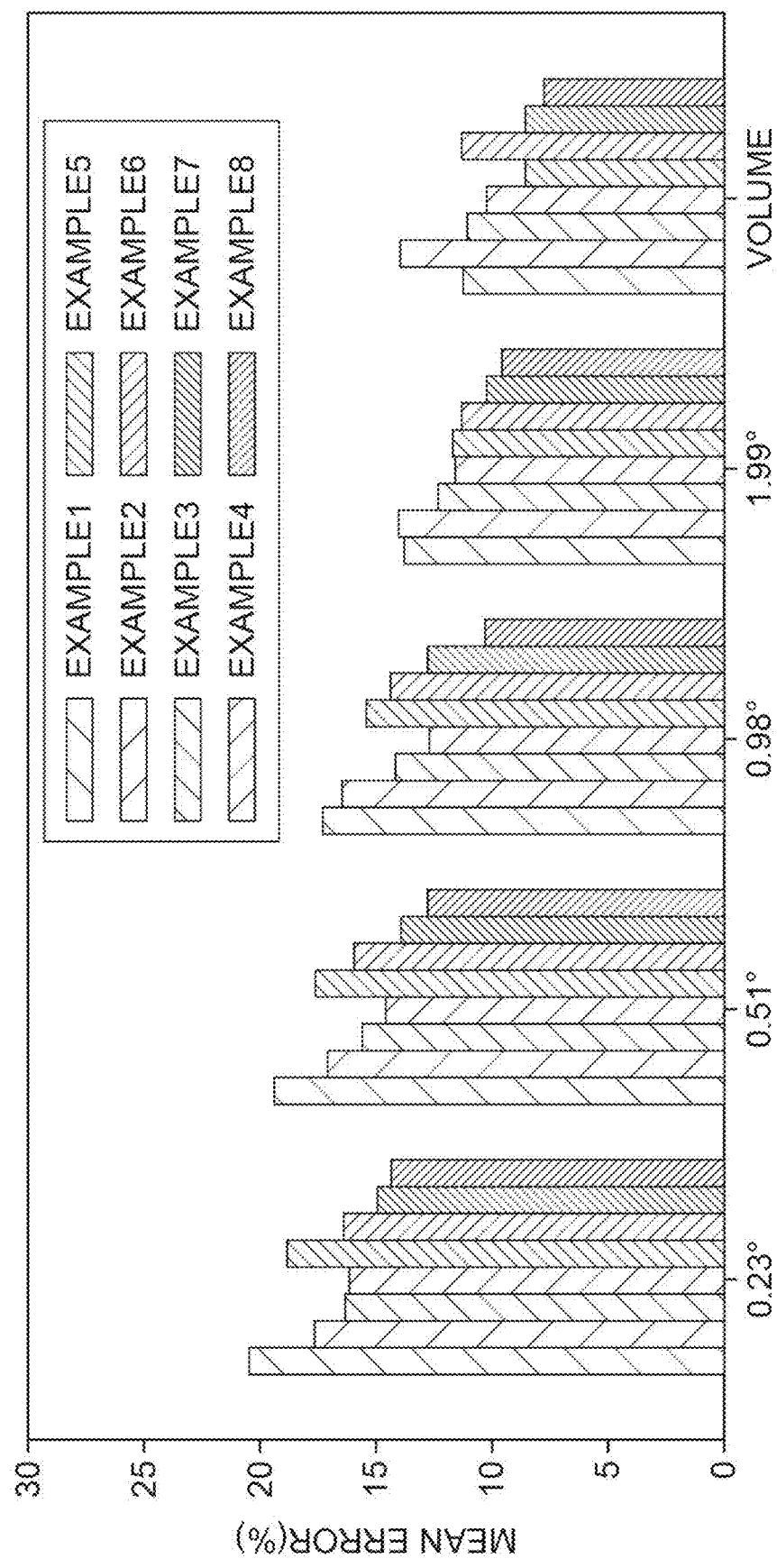
FIG. 9 is a graph illustrating a result of an experiment on accuracy of an MPOD numerical value sequence predicted in the embodiment.

FIG. 9 illustrates mean errors of numerical values included in an MPOD numerical value sequence in a case in which only a second ocular fundus image is used as a 1ch input image and an ensemble process is not performed (Example 1), a case in which only a difference image is used as a 1ch input image and an ensemble process is not performed (Example 2), a case in which only a first ocular fundus image is used as a 1ch input image and an ensemble process is not performed (Example 3), a case in which 3ch input images are used and an ensemble process is not performed (Example 4), a case in which only a second ocular fundus image is used as a 1ch input image and an ensemble process is performed (Example 5), a case in which only a difference image is used as a 1ch input image and an ensemble process is performed (Example 6), a case in which only a first ocular fundus image is used as a 1ch input image and an ensemble process is performed (Example 7), and a case in which 3ch input images are used and an ensemble process is performed (Example 8). From these results of experiment, it can be seen that an error using 3ch inputs decreases in both cases in which an ensemble process is performed and not performed. It can also be seen that the error is smallest when an ensemble process is performed with 3ch inputs. From these results, it can be seen that both the 3ch inputs and the ensemble process are important to decrease an error of predicted values.

While various embodiments of the present invention have been described above, the present invention is not limited to the embodiments, but may be modified or applied to other configurations without departing from the gist described in the appended claims.

The image input unit 3 of the ocular fundus image processing device 1 according to the embodiment acquires a difference image on the basis of an ocular fundus image set of a prediction target and a pre-surgery ocular fundus image set and uses the difference image in the training phase and the prediction phase. In a modified example, an addition image obtained by adding luminance values of pixels between the first ocular fundus image and the second ocular fundus image may be acquired on the basis of the ocular fundus image sets, and the addition images may be used in the training phase and the prediction phase.

The coefficient deriving unit 11 of the ocular fundus image processing device 1 according to the embodiment calculates a mean value as a statistical value of three CF numerical value sequences, but may calculate a median value. In this case, it is possible to predict a quantity of macular pigment with high accuracy.

A configuration of a deep learning model for predicting a CF numerical value sequence used in the ocular fundus image processing device 1 according to the embodiment is not limited to the configuration illustrated in FIG. 3. For example, a configuration of a trained model LM illustrated in FIG. 10 may be used.

Figure 10:
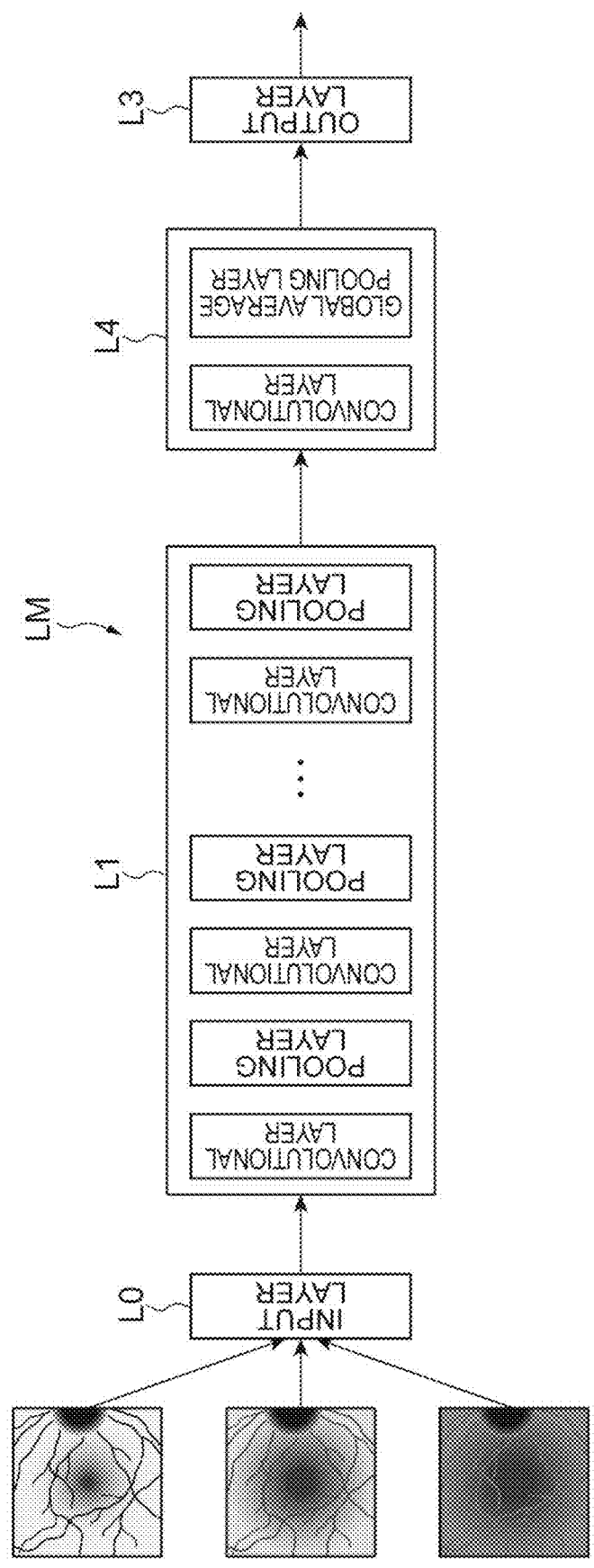
FIG. 10 is a diagram illustrating a network structure of a trained model LM which is used in a modified example.

The trained model LM illustrated in FIG. 10 has a configuration in which a convolutional layer and a global average pooling layer are connected in this order as the subsequent-stage structure L4 connected to the preceding-stage structure L1. Parameters trained already (such as parameters of a weighting filter) are used as initial values in the parameters of the trained model LM with the aforementioned structure, except for the convolutional layer in the subsequent-stage structure L4.

Figure 11:
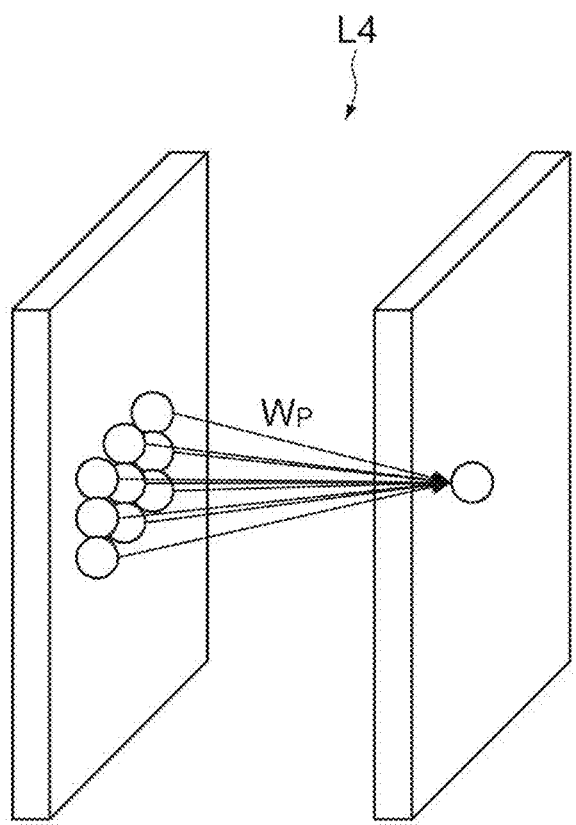
FIG. 11 is a diagram illustrating a connecting configuration of two layers in a subsequent-stage structure L5 of the trained model LM illustrated in FIG. 10.

In a modified example in which the configuration of the trained model LM illustrated in FIG. 10 is employed, the model generating unit 7 randomly changes the initial values of the parameters of the convolutional layers in the subsequent-stage structure L4 on the basis of a pseudo-random number sequence. Specifically, as illustrated in FIG. 11, the model generating unit 7 sets the initial value of the weighting factor $w_p$ of a filter which is applied to the convolutional layer in the subsequent-stage structure L4 according to the pseudo-random number sequence. According to this modified example, it is possible to comprehensively generate a plurality of deep learning models for predicting the CF numerical value sequences.

In the aforementioned embodiment, one of the first wavelength and the second wavelength may be a wavelength in the blue wavelength band, and the other of the first wavelength and the second wavelength may be a wavelength in the green wavelength band. Since a yellow spot has characteristics of absorbing blue light, it is possible to calculate a quantity of macular pigment with high accuracy by using two images based on excitation light of such wavelengths as input images.

The input images may further include a difference image or an addition image based on the first image and the second image. In this case, since a difference image or an addition image based on two images is included in the input images, it is possible to calculate a quantity of macular pigment with higher accuracy.

The statistical value may be a mean value or median value of the plurality of correction factors. In this case, since the quantity of macular pigment can be calculated such that a plurality of correction factors predicted using a plurality of trained deep learning models are equally reflected, it is possible to calculate a quantity of macular pigment with higher reliability.

In the aforementioned embodiment, the pseudo-random numbers generated on the basis of a plurality of different initial values may be used to train the deep learning models. With this configuration, it is possible to comprehensively generate a plurality of deep learning models for predicting the correction factors even when training is performed using a restricted number of input images.

In the aforementioned embodiment, the pseudo-random numbers may be used to initialize parameters of a deep learning model. The order of input images which are input to the deep learning model may be changed on the basis of the pseudo-random numbers. With this configuration, it is possible to comprehensively generate a plurality of deep learning models for predicting the correction factors even when training is performed using a restricted number of input images.

INDUSTRIAL APPLICABILITY

The embodiment is applicable to an ocular fundus image processing method, an ocular fundus image processing device, an ocular fundus image processing program, and a recording medium storing the program, and enables deriving an MPOD with high reliability through a simple process.

REFERENCE SIGNS LIST

1 Ocular fundus image processing device
P1 Ocular fundus image processing program
3 Image input unit (first acquisition unit, second acquisition unit)
7 Model generating unit
9 Coefficient predicting unit
11 Coefficient deriving unit
13 Pigment quantity calculating unit
20 Computer
101 CPU (processor)
LM Trained model

The invention claimed is:

1. An ocular fundus image processing method comprising:
acquiring a first image which is a fluorescence image of an ocular fundus of a subject generated by irradiating the ocular fundus with excitation light of a first wavelength;
acquiring a second image which is a fluorescence image of the ocular fundus of the subject generated by irradiating the ocular fundus with excitation light of a second wavelength different from the first wavelength;
generating a plurality of trained deep learning models for predicting a correction factor for calculating a quantity of macular pigment of the subject from input images including at least the first image and the second image through training using a plurality of different initial values;
predicting a plurality of correction factors by inputting the input images including at least the first image and the second image to the plurality of trained deep learning models;
calculating a statistical value of the plurality of correction factors and deriving the statistical value as the correction factor of the subject; and
calculating a quantity of macular pigment of the subject on the basis of at least one of the first image and the second image and the correction factor of the subject.

2. The ocular fundus image processing method according to claim 1, wherein one of the first wavelength and the second wavelength is a wavelength in a blue wavelength band, and the other of the first wavelength and the second wavelength is a wavelength in a green wavelength band.

3. The ocular fundus image processing method according to claim 1, wherein the input images further include a difference image or an addition image based on the first image and the second image.

4. The ocular fundus image processing method according to claim 1, wherein the statistical value is a mean value or median value of the plurality of correction factors.

5. The ocular fundus image processing method according to claim 1, wherein the step of generating a plurality of trained deep learning models includes training deep learning models using pseudo-random numbers which are generated on the basis of the plurality of different initial values.

6. The ocular fundus image processing method according to claim 5, wherein generating a plurality of trained deep learning models includes using the pseudo-random numbers to initialize parameters of the deep learning model.

7. The ocular fundus image processing method according to claim 5, wherein generating a plurality of trained deep learning models includes changing the order of input images which are input to the deep learning model on the basis of the pseudo-random numbers.

8. An ocular fundus image processing device comprising:
a circuitry configured to
acquire a first image which is a fluorescence image of an ocular fundus of a subject generated by irradiating the ocular fundus with excitation light of a first wavelength,
acquire a second image which is a fluorescence image of the ocular fundus of the subject generated by irradiating the ocular fundus with excitation light of a second wavelength different from the first wavelength,
generate a plurality of trained deep learning models for predicting a correction factor for calculating a quantity of macular pigment of the subject from input images including at least the first image and the second image through training using a plurality of different initial values,
predict a plurality of correction factors by inputting the input images including at least the first image and the second image to the plurality of trained deep learning models,
calculate a statistical value of the plurality of correction factors and to derive the statistical value as the correction factor of the subject, and
calculate a quantity of macular pigment of the subject on the basis of at least one of the first image and the second image and the correction factor of the subject.

9. The ocular fundus image processing device according to claim 8, wherein one of the first wavelength and the second wavelength is a wavelength in a blue wavelength band, and the other of the first wavelength and the second wavelength is a wavelength in a green wavelength band.

10. The ocular fundus image processing device according to claim 8, wherein the input images further include a difference image or an addition image based on the first image and the second image.

11. The ocular fundus image processing device according to claim 8, wherein the statistical value is a mean value or median value of the plurality of correction factors.

12. The ocular fundus image processing device according to claim 8, wherein the circuitry is configured to train deep learning models using pseudo-random numbers which are generated on the basis of the plurality of different initial values.

13. The ocular fundus image processing device according to claim 12, wherein the circuitry is configured to use the pseudo-random numbers to initialize parameters of the deep learning model.

14. The ocular fundus image processing device according to claim 12, wherein the circuitry is configured to change the order of input images which are input to the deep learning model on the basis of the pseudo-random numbers.

15. An ocular fundus image processing program causing a processor function as steps of:

acquiring a first image which is a fluorescence image of an ocular fundus of a subject generated by irradiating the ocular fundus with excitation light of a first wavelength;

acquiring a second image which is a fluorescence image of the ocular fundus of the subject generated by irradiating the ocular fundus with excitation light of a second wavelength different from the first wavelength;

generating a plurality of trained deep learning models for predicting a correction factor for calculating a quantity of macular pigment of the subject from input images including at least the first image and the second image through training using a plurality of different initial values;

predicting a plurality of correction factors by inputting the input images including at least the first image and the second image to the plurality of trained deep learning models;

calculating a statistical value of the plurality of correction factors and to derive the statistical value as the correction factor of the subject; and calculating a quantity of macular pigment of the subject on the basis of at least one of the first image and the second image and the correction factor of the subject.

16. A computer-readable recording medium storing the ocular fundus image processing program according to claim 15.

\* \* \* \* \*